(12) United States Patent
Bryant-Greenwood et al.

(10) Patent No.: US 7,524,636 B2
(45) Date of Patent: Apr. 28, 2009

(54) METHODS FOR DIAGNOSING LABOR

(75) Inventors: Gillian D. Bryant-Greenwood, Honolulu, HI (US); Lily S. Tashima, Honolulu, HI (US); Simona Ognjanovic, Aiea, HI (US); Elizabeta Nemeth, Los Angeles, CA (US); Lynnae K. Millar, Kaneohe, HI (US)

(73) Assignee: University of Hawaii, Honolulu, HI (US)

(*) Notice: Subject to any disclaimer, the term of this patent is extended or adjusted under 35 U.S.C. 154(b) by 393 days.

(21) Appl. No.: 11/112,659

(22) Filed: Apr. 22, 2005

(65) Prior Publication Data
US 2005/0260683 A1 Nov. 24, 2005

Related U.S. Application Data

(63) Continuation-in-part of application No. PCT/US03/033983, filed on Oct. 23, 2003.

(60) Provisional application No. 60/420,975, filed on Oct. 23, 2002.

(51) Int. Cl.
G01N 33/53 (2006.01)
(52) U.S. Cl. .................... 435/7.1; 530/351; 530/851
(58) Field of Classification Search .............. None
See application file for complete search history.

(56) References Cited

U.S. PATENT DOCUMENTS

| | | | |
|---|---|---|---|
| 4,160,452 A | 7/1979 | Theeuwes | |
| 4,256,108 A | 3/1981 | Theeuwes | |
| 4,265,874 A | 5/1981 | Bonsen et al. | |
| 5,516,702 A * | 5/1996 | Senyei et al. | 436/510 |
| 2002/0164656 A1* | 11/2002 | Hoeffler et al. | 435/7.2 |

OTHER PUBLICATIONS

Fried et al., 2003, Molecular Human Reproduction, 9: 719-724.*
Whittle et al., 2000, Placenta 21: 394-401.*
Pribyl et al., 2003, Biophysical Journal 84: 3624-3635.*
Rongvaux et al., 2002, European Journal of Immunology 32:3 225-3234.*
Ben-Jonathan et al. 2008: Endocrine Reviews 29: 1-41.*
Goldenberg et al. 2008, Lancet 371: 75-84.*
Bryant-Greenwood et al. 2007, Reproductive Sciences 14: 42-45.*
Sadowsky et al. 2006, American Journal of Obstetrics and Gynecology 195: 1578-1589.*
Shim et al., 2004, American Journal of Obstetrics and Gynecology 191:1339-1345.*
Luk et al. 2008, Journal of Leukocyte Biology 83, e-publication as DOI: 10.1189/jib.0807581, published ahead of printed version.*
Tanaka et al. 2007, Biochemical and Biophysical Research Communications 359:194-201.*
Brentano et al., 2007: Arthritis and Rheumatism 56: 2829-2839.*
Ognjanovic et al. 2003, Amer J Obstet Gynecol 189:1187-1195.*
Yeast and Lu, 2007, Clinics in Perinatology 34: 573-586.*

Arici et al. "Interleukin-8 induces proliferation of endometrial stromal cells: a potential autocrine growth factor." in J Clin Endocrinol Metab 1998; 83:1201-5.
Aviv H and Leder P. "Purification of biologically active globin mRNA by chromatography on oligothymidylic acid-cellulose." in PNAS 1972; 62:1408-12.
Chomzynski P and Sacchi N. "Single step method of RNA isolation by acid guanidinium thiocyanate-phenyl-chloroform extraction." in Anal Biochem 1987; 162:159-69.
Dudley DJ. "Immunoendocrinology of preterm labor: the link between corticotropin-releasing hormone and inflammation." in Am J Obstet Gynecol 1999; 180: S251-6.
Elliot et al., "IL-1β and IL-8 in human fetal membranes: changes with gestational age, labor and culture conditions." in Amer. J. Reprod. Immun. 2001;46:260-7.
Goldenberg et al., "Intrauterine infection and preterm delivery." in New Engl J Med 2000 342:1500-1507.
Keelan et al., "Regulation of interleukin-6 and interleukin-8 production in an amnion-derived cell line by cytokines, growth factors, glucocorticoids and phorbol esters." in Am J Reprod Imm 1997;38:272-278.
Laham et al. "Interleukin-8 release from human gestational tissue explants: the effects of lipopolysaccharide and cytokines." in Biol. Reprod. 1997; 57:616-620.
Laham et al., "Interleukin-8 release from human gestational tissue explants: effects of gestation, labor and chorio-amnionitis." in Biol Reprod 1999;61:823-827.
Laham et al., "Differential release of interleukin-6 from human gestational tissues in association with labor and in vitro endotoxin treatment." in J Endocrinol 1996;146:431-439.
Mauldin JG and Newman RB. "Preterm birth risk assessment." in Semin Perinatol 2001;4:215-222.
Millar et al., "A relaxin-mediated pathway to the preterm premature rupture of the fetal membranes, independent of infection." in Am J Obstet Gynecol 1998;179:126-134.
Mitchell et al., "Interleukin-6 stimulates prostaglandin production by human amnion and decidual cells." in Eur J Pharm 1991;192:189-191.

(Continued)

*Primary Examiner*—Michael Szperka
(74) *Attorney, Agent, or Firm*—Foley & Lardner LLP; Stephen E. Reiter

(57) ABSTRACT

In accordance with the present invention, recombinant human PBEF has been produced in order to study its ability to stimulate the transcription of the key cytokine mediators of labor induction, using the amnion-like epithelial (WISH) cell line and fetal membrane explants. As a result of these studies, it has been determined that PBEF is a good indicator of initiation of labor. This makes PBEF a useful marker, especially for the identification of subjects who have initiated preterm labor. Accordingly, methods for the identification of subjects who have commenced labor are provided. In addition, methods are also provided for blocking labor, as well as compositions useful therefor. This is accomplished by blocking the production of PBEF or by blocking the action of PBEF.

10 Claims, 6 Drawing Sheets

OTHER PUBLICATIONS

Naeye RI. "Disorders of the placenta, fetus and neonate: diagnosis and clinical significance." Chapter 8. Methods of Preparing Sections of Microscopic Examination. St Louis: CU Mosby; 1992. p. 258.

Nemeth et al., "Fetal membrane distension: II. Differentially expressed genes regulated by acute distension in vitro." in Am J Obstet Gynecol 2000; 182:60-67.

Nemeth et al., "Fetal membrane distension I. Differentially expressed genes regulated by acute distension in amniotic epithelial (WISH) cells." in Am J Obstet Gynecol 2000; 192:50-59.

Ognjanovic et al., "Pre-B-cell colony-enhancing factor is a secreted cytokine-like protein from the uman amniotic epithelium." American Journal of Obstetrics and Gynecology, 2005, 193:273-282.

Ognjanovic et al., "Genomic organization of the gene coding for human pre-B cell colony-enhancing factor and expression in human fetal membranes." in J Mol Endocrinol 2001;26:107-117.

Opsjon et al. "Tumor necrosis factor, interleukin-1 and interleukin-6 in normal human pregnancy." in Am J Obstet Gynecol 1993;169:397-404.

Osmers et al., "Interleukin-8 synthesis and the onset of labor." in Obstet Gynecol 1995;86:223-229.

Romero et al. "Neutrophil attractant/activating peptide-1/interleukin-8 in term and preterm parturition." in Am J Obstet Gynecol 1991;165:813-820.

Samal et al., "Cloning and characterization of the cDNA encoding a novel human pre-B-cell colony-enhancing factor." in Mol Cell Biol 1994;14:1431-1437.

Winkler et al. "Collagenolysis in the lower uterine segment during parturition at term: correlations with stage of cervical dilatation and duration of labor." in Am J Obstet Gynecol 1999:181:153-158.

* cited by examiner

METHODS FOR DIAGNOSING LABOR

RELATED APPLICATIONS

This application claims benefit of PCT US03/33983, filed Oct. 23, 2003, which, in turn, claims priority from U.S. Application No. 60/420,975, filed Oct. 23, 2002, the entire contents of each of which are hereby incorporated by reference herein.

FIELD OF THE INVENTION

The present invention relates to methods for diagnosing and treating preterm labor. In another aspect, the present invention relates to methods for determining whether a subject has commenced labor. In a further aspect, the present invention relates to methods for stimulating cytokine production.

BACKGROUND OF THE INVENTION

Preterm birth is a multifactorial disease involving activation of uterine contractions and/or decreased cervical competence, which can be the result of an inflammatory, infectious or ischemic insult to the uteroplacental barrier (see Mauldin J G and Newman R B. "Preterm birth risk assessment." in Semin Perinatol 2001;4:215-22). Preterm labor, defined as uterine contractions or preterm premature rupture of the fetal membranes before 37 weeks gestational age, accounts for some 80% of all preterm deliveries (see Goldenberg R, Hauth J C, and Andrews W W. "Intrauterine infection and preterm delivery." in New Engl J Med 2000:342:1500-7). There is little doubt that cytokine secretion by inflammatory cells plays an important role in the initiation of infection-induced parturition (see Dudley D J. "Immunoendocrinology of preterm labor: the link between corticotropin-releasing hormone and inflammation." in Am J Obstet Gynecol 1999; 180: S251-6). It seems likely that IL-6 (see Opsjon et al. "Tumor necrosis factor, interleukin-1 and interleukin-6 in normal human pregnancy." in Am J Obstet Gynecol 1993;169:397-404) and IL-8 (see Arici et al. "Interleukin-8 induces proliferation of endometrial stromal cells: a potential autocrine growth factor." in J Clin Endocrinol Metab 1998;83:1201-5) are also involved in the normal localized growth required for successful pregnancy. However, their involvement in normal parturition appears to be facilitative rather than initiative. Thus, in the absence of chorioamnionitis, as the cervix dilates, there is increased contact between the decidua/fetal membranes and the upper genital tract. This contact results in the locally increased production of several inflammatory cytokines, albeit at lower concentrations than in infection-induced parturition, and this augments and drives both uterine contraction and further cervical dilatation via the induction of prostaglandins (see Mitchell M D, Dudley D J, Edwin S S and Lundin-Schiller S. "Interleukin-6 stimulates prostaglandin production by human amnion and decidual cells." in Eur J Pharm 1991;192:189-91) and matrix metalloproteinases (see Winkler M, Oberpichler A, Tschetsche H, Ruck P, Fischer D C and Rath W. "Collagenolysis in the lower uterine segment during parturition at term: correlations with stage of cervical dilatation and duration of labor." in Am J Obstet Gynecol 1999:181:153-8). In this manner, both an inflammatory response and decidual activation are initiated and/or augmented, accelerating the subsequent events leading to birth.

Pre-B-cell colony enhancing factor (PBEF) was first identified from activated peripheral blood lymphocytes and shown to be involved in the maturation of B-cell precursors (see Samal B, Sun Y, Stearns G, Xie C, Suggs S and McNiece I. "Cloning and characterization of the cDNA encoding a novel human pre-B-cell colony-enhancing factor." in Mol Cell Biol 1994; 14:1431-7). In studying the effects of acute distension on the genes expressed by human amniotic epithelial cells (WISH), one of these genes was identified as PBEF (see Nemeth E, Tashima L S, Yu Z and Bryant-Greenwood G D. "Fetal membrane distension I. Differentially expressed genes regulated by acute distension in amniotic epithelial (WISH) cells." in Am J Obstet Gynecol 2000;192:50-9; referred to hereinafter as "Nemeth I"). When preterm and term full-thickness fetal membranes were similarly distended in vitro, it was shown that the expression of the PBEF gene was greater in the preterm than in the term membranes (see Nemeth E, Millar L K and Bryant-Greenwood G. "Fetal membrane distension: II. Differentially expressed genes regulated by acute distension in vitro." in Am J Obstet Gynecol 2000; 182:60-7; referred to hereinafter as "Nemeth II"). This suggested that by term, the tissue had attained its maximum distension, and sensitivity to further distension was then limited. While distension is a part of the normal process of pregnancy, uterine contractions also cause distension, thus distension is also a key part of the labor process.

A genomic clone of PBEF was subsequently analysed and shown to be a highly regulated gene. An important finding in this study was the identification of an NF-κB binding element in the third intron, likely to be responsible for the responsiveness to distension (see Ognjanovic S, Bao S, Yamamoto S Y, Garibay-Tupas J, Samal B, and Bryant-Greenwood G D. "Genomic organization of the gene coding for human pre-B cell colony-enhancing factor and expression in human fetal membranes." in J Mol Endocrinol 2001;26:107-117). PBEF was also localized with a specific antiserum, showing that the expression of the PBEF gene was significantly upregulated in severely infected membranes. In addition, the neutrophils present in these tissues stained darkly for PBEF, suggesting that they are an additional source of PBEF in the setting of infection (see Ognjanovic et al., supra). However, while LPS, TNF-α, IL-1β and IL-6 all induced PBEF gene expression, it has been shown that IL-8 treatment had no such effect (see Ognjanovic et al., supra). This was particularly interesting because IL-8 and PBEF expression both increased when WISH cells and the fetal membranes were acutely distended (see Nemeth I and Nemeth II, supra). Therefore, like PBEF, IL-8 appears to be responsive to distension in a sterile situation, as well as being induced by infection, but its relationship with PBEF under these conditions is unknown.

PBEF is present in fetal membranes during normal gestation and parturition in the absence of infection. Its expression increases with both preterm labor and normal labor at term. Moreover, PBEF causes an increase in the expression in fetal membranes of many key proteins that are known activators of the labor process (see, for example, FIG. 5). Thus, it was investigated whether PBEF could serve as a useful marker for identifying patients in true labor, providing new diagnostic modalities not previously available. Furthermore, it was investigated whether the action of PBEF could be blocked, or its expression blocked, thereby stopping the labor process and providing new treatment modalities not previously available.

SUMMARY OF THE INVENTION

In accordance with the present invention, recombinant human PBEF has been produced in order to study its ability to stimulate the transcription of the classical cytokines, e.g., TNF-α, IL-6 and IL-8, using the amnion-like epithelial (WISH) cell line and fetal membrane explants. As a result of these studies, it has been determined that PBEF is a good indicator of the initiation of labor. This makes PBEF a useful marker, especially for the identification of subjects who have initiated preterm labor. Accordingly, methods for the identification of subjects who have commenced labor are provided. In addition, methods are also provided for blocking labor, as well as compositions useful therefor. This is accomplished by blocking the production of PBEF or by blocking the action of PBEF.

BRIEF DESCRIPTION OF THE FIGURES

The several panels of FIG. 1 collectively illustrate examples of immunostaining for PBEF in human fetal membranes. Thus, PBEF protein was immunolocalized to the human fetal membranes obtained early in pregnancy (day 87), at preterm and after term spontaneous labor and delivery.

The several panels of FIG. 3 collectively illustrate the expression of PBEF, IL-6 and IL-8 in the human fetal membranes: open bar: no labor, solid bar: labor.

The several panels of FIG. 4 collectively illustrate the effect of rhPBEF treatment on the expression of IL-6 and IL-8 in amniotic epithelial (WISH) cells.

DETAILED DESCRIPTION OF THE INVENTION

Figure 1A:
FIG. 1A illustrates immunostaining for PBEF in a consistent and uniform manner in the fetal membranes obtained in early pregnancy (87 days gestation). Good staining was obtained in the amniotic epithelium (a) and mesenchymal (m) cells of the amniotic connective tissue in each tissue studied. A consecutive section was used as a control with IgG derived from non-immune rabbit serum at the same concentration as anti-PBEF in FIG. 1A (see FIG. 1B).
Figure 1B:
FIG. 1C illustrates the fetal membranes from patients delivered preterm, after labor, showing positive staining for PBEF (which was also uniform over each section), with no evidence of chorioamnionitis. The staining was primarily in the amniotic epithelium (a), with good staining also in the cells of the chorionic cytotrophoblast (c) and the parietal decidua. The decidual cells are not easily seen in this section, but also stained quite well.
FIG. 1D illustrates normal fetal membranes from a term spontaneous labor and vaginal delivery showing good staining in the amniotic epithelial cells, which appeared to be perinuclear in many cells. The mesenchymal cells (m) embedded in the connective tissue of the amnion and chorion were quite prominently stained in this section. There was also uniform staining of the cytoplasm of the cells of the chorionic cytotrophoblast and the decidua; the latter is not seen in this section.
Figure 1C:
Figure 1D:
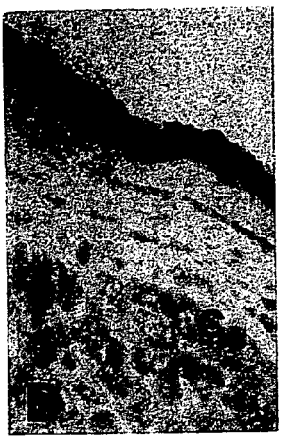

In accordance with the present invention, there are provided methods for determining whether a subject has commenced labor, said methods comprising assaying for the level of pre-B cell colony-enhancing factor (PBEF) in one or more of the serum, cervical fluid, vaginal fluid and amniotic fluid of said subject, and identifying a subject whose level of PBEF is elevated above baseline as having commenced labor. Invention methods are useful in a variety of circumstances, especially when the subject being tested is suspected of having commenced preterm labor.

As readily recognized by those of skill in the art, the level of PBEF can be assayed in a variety of ways, e.g., by immunoassay, by lysate array, by chromatographic analysis, by mass spectrometric analysis, and the like. Such techniques are well known in the art and can be readily carried out by those of skill in the art.

The sensitivity of the above-described assay methods can be further enhanced by employing such highly sensitive detection techniques as colorometric analysis, fluorescent analysis, radioassays using radiolabelled substrates, and the like.

The above-described assays can be carried out together with other diagnostic tests, with positive results in both tests being confirmatory of the conclusion that the subject has commenced labor. Such additional tests include determination of vaginal fetal fibronectin, cervical length measurements, uterine contraction monitoring, and the like.

In accordance with another embodiment of the present invention, there are provided methods of blocking labor in a subject in need thereof, said methods comprising blocking the action of pre-B cell colony-enhancing factor (PBEF) in said subject.

As readily recognized by those of skill in the art, the action of PBEF can be blocked in a variety of ways, e.g., by administration of an anti-PBEF antibody, by administration of a PBEF antagonist, and the like. In addition to administration of one or more of the above-mentioned agents, in accordance with another aspect of the present invention, one or more anti-labor drugs (e.g., anti-cytokines, anti-prostaglandins, anti-oxytocin, anti-inflammatory agents, and the like) can be administered in combination with said agent which blocks the action of PBEF.

Depending on the mode of delivery employed, the compounds contemplated for use herein can be delivered in a variety of pharmaceutically acceptable forms. For example, invention compounds can be delivered in the form of a solid, solution, emulsion, dispersion, micelle, liposome, and the like.

Thus, in accordance with still another embodiment of the present invention, there are provided pharmaceutical formulations comprising invention compounds in a suitable vehicle rendering said compounds amenable to oral delivery, transdermal delivery, intravenous delivery, intramuscular delivery, topical delivery, nasal delivery, and the like.

Pharmaceutical compositions of the present invention can be used in the form of a solid, a solution, an emulsion, a dispersion, a micelle, a liposome, and the like, wherein the resulting composition contains one or more of the compounds of the present invention as an active ingredient, in admixture with an organic or inorganic carrier or excipient suitable for enteral or parenteral applications. Invention compounds may be compounded, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,160,452; and 4,265,874, to form osmotic therapeutic tablets for controlled release.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin, or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Compounds contemplated for use in the practice of the present invention may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquify and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner. In general, the dosage of invention compounds employed as described herein falls in the range of about 0.01 mmoles/kg body weight of the subject/hour up to about 0.5 mmoles/kg/hr. Typical daily doses, in general, lie within the range of from about 10 µg up to about 100 mg per kg body weight, and, preferably within the range of from 50 µg to 10 mg per kg body weight and can be administered up to four times daily. The daily IV dose lies within the range of from about 1 µg to about 100 mg per kg body weight, and, preferably, within the range of from 10 µg to 10 mg per kg body weight.

As an alternative to blocking the action of PBEF, in accordance with another aspect of the present invention, the effect of PBEF can be blocked by blocking the production of PBEF. This can be accomplished in a variety of ways, e.g., by administration of antisense oligonucleotide, which has a sequence which has been derived from the PBEF coding sequence. In addition, in accordance with another aspect of the present invention, one or more blocking agents or mediators of labor can be administered in combination with said agent which blocks the production of PBEF.

In accordance with still another embodiment of the present invention, there are provided methods for determining whether a test compound blocks pre-B cell colony-enhancing factor (PBEF) production, said methods comprising assaying test cells for PBEF production when said cells are contacted with test compound, wherein test cells comprise human amniotic epithelial cells treated with lipopolysaccharide, TNF-α and/or IL-1β.

As readily recognized by those of skill in the art, PBEF production can be assayed in a variety of ways, e.g., by immunoassay, by Northern analysis, by lysate array, and the like. Such techniques are well known in the art and can be readily carried out by those of skill in the art.

In accordance with a further embodiment of the present invention, there are provided methods for determining whether a test compound blocks the action of pre-B cell colony-enhancing factor (PBEF), said methods comprising assaying test cells for cytokine production when said cells are contacted with test compound, wherein test cells comprise amnion-like epithelial cell lines or fetal membrane explants treated with lipopolysaccharide.

The production of a variety of cytokines can be assayed in accordance with the present invention, such as, for example, tumor necrosis factor-alpha (TNF-α), interleukin-1-beta (IL-1 β), interleukin-6 (IL-6), interleukin-8 (IL-8), and the like.

As readily recognized by those of skill in the art, cytokine production can be assayed in a variety of ways, e.g., by immunoassay, by Northern analysis, by lysate array, and the like. Such techniques are well known in the art and can be readily carried out by those of skill in the art.

In accordance with a still further embodiment of the present invention, there are provided methods for stimulating cytokine production in fetal membranes, said methods comprising contacting said membrane with an effective amount of pre-B cell colony-enhancing factor (PBEF).

In this disclosure, it is shown that PBEF is constitutively expressed in the fetal membranes and placenta during normal gestation with no marked increase with gestational age. In this respect, PBEF appears to be like IL-8, which is also constitutively expressed and has been suggested to have a physiological role during normal gestation (see Osmers R G W, Blaser J, Kuhn W, and Tschesche H. "Interleukin-8 synthesis and the onset of labor." in Obstet Gynecol 1995;86: 223-9). However, PBEF causes the increased expression of many key proteins that are known activators of the labor process. Thus, PBEF is at the apex of the sequence of events leading to preterm labor.

In patients with no chorioamnionitis, it has been shown that IL-6 gene expression was significantly increased by labor at both preterm and term, with a greater increase at preterm than term. This agrees with previously published data (see, for example, Laham N, Brennecke S P, Bendtzen K, and Rice G E. "Differential release of interleukin-6 from human gestational tissues in association with labor and in vitro endotoxin treatment." in J Endocrinol 1996; 146:431-9; and Laham N, Brennecke S P and Rice G E. "Interleukin-8 release from human gestational tissue explants: effects of gestation, labor and chorio-amnionitis." in Biol Reprod 1999;61:823-7). The expression of IL-8, on the other hand, significantly increased only with labor at term, also agreeing with published work (see, for example, Romero R, Ceska M, Avila C, Mazor M, Behnke E and Lindley I. "Neutrophil attractant/activating peptide-1/interleukin-8 in term and preterm parturition." in Am J Obstet Gynecol 1991;165:813-20; and Elliot C L, Loudon J A Z, Brown N, Slater D M, Bennet P R and Sullivan M H F. "IL-1β and IL-8 in human fetal membranes: changes with gestational age, labor and culture conditions." in Amer. J. Reprod. Immun. 2001 ;46:260-7). However, PBEF expression showed increases to approximately the same levels with labor at both preterm and term, with neither reaching a level of significance compared to the non-labored controls. This was apparently due to the considerably greater variation in the expression of PBEF in the non-labored patients, which was not the case for either IL-6 or IL-8. Greater sample numbers may have shown a significant effect of labor on PBEF gene expression in the fetal membranes.

Recombinant human PBEF (rhPBEF) was produced in order to study the relationship of PBEF with other key cytokines and proteins, which are known to be inducers of uterine contractions and/or cervical dilatation. In one study which involved adding PBEF to either WISH cells or explants of fetal membrane, it was shown that PBEF increased the expression of MRNA for IL-6 in a dose-dependent manner (see Ognjanovic et al., supra). In explants, PBEF increased the expression of the IL-6 gene by 40%, which approximated the maximal effect of PBEF (44%) in WISH cells. In a similar way it was shown that PBEF caused a 120% increase in the expression of IL-8 in fetal membrane explants.

The proinflammatory cytokines TNF-A and IL-1β have been shown to stimulate IL-6 (see Keelan J A, Sato T, and Mitchell M D. "Regulation of interleukin-6 and interleukin-8 production in an amnion-derived cell line by cytokines, growth factors, glucocorticoids and phorbol esters." in Am J Reprod Imm 1997;38:272-8), IL-8 (see, for example, Keelan et al., supra; and Laham N Brennecke S P and Rice G E. "Interleukin-8 release from human gestational tissue explants: the effects of lipopolysaccharide and cytokines." in Biol. Reprod. 1997; 57:616-20) and PBEF (see Ognjanovic et al., supra) transcription. It is demonstrated herein that rhPBEF stimulates the expression of TNF-α, IL-1β, IL-6, and cyclooxygenase-2 (COX-2) gene expression in the fetal membranes. This clearly places PBEF at the upstream point of the known pathway to labor, at preterm or term (see FIG. 6). These studies were conducted with rhPBEF addition to explants of fetal membranes and the RNA from treated and control (untreated) tissue used for isolation of total RNA and hybridization to DNA microchips (Affymetrix Inc.). Computer analysis of the signals identified 7 genes in the labor cascade which were upregulated in the fetal membranes by their treatment with rhPBEF, in all patients studied. This has been confirmed in both tissue from other patients and by measurement of the respective secreted proteins in addition to the expression of the genes in the tissues. Thus, PBEF is an initiator of the cascade of events currently recognized as leading to labor and delivery.

The invention will now be described in greater detail by reference to the following non-limiting examples.

EXAMPLE 1

Materials

Tissues for immunolocalization. Early pregnancy fetal membranes (87, 94 and 101 days gestation) were obtained after elective pregnancy termination and were kindly supplied by the Department of Pediatrics, University of Washington, Seattle. These tissues were dated by the day of the last menstrual period and collected within an hour of termination. They were collected with approval by the human subjects ERB of the University of Washington and shipped to Hawaii for use with no patient identification. Placentas and fetal membranes were also collected as soon as possible after delivery at Kapiolani Medical Center for Women and Children (Honolulu, Hi.) with informed consent and approval from the University Committee on Human Experimentation and the Hospital Institutional Review Board. These tissues were from patients after spontaneous preterm labor at 28-37 weeks gestation (n=4) and after normal spontaneous labor at term, 40-42 weeks gestation (n=4). Small pieces (3×3 cm) were rolled from each membrane and placed in Bouin's fixative for 18 h at room temperature.

Tissues for Northern analysis. Placentas and fetal membranes were obtained from patients after elective Cesarean section at term before labor (38-40 weeks gestation, n=5), placed on ice and the layers separated by scraping the decidua from the chorionic surface with a blunt glass slide, and by stripping the amnion from other surface of the chorion. The samples of placenta were cut from the villous trophoblast in the center of the tissue avoiding the chorionic and basal plates. Samples were frozen separately in liquid nitrogen: however, three of the decidual samples were of inadequate weight and were therefore pooled (n=3). Total RNA was isolated from the samples using the method of Chomzynski (see Chomzynski P and Sacchi N. "Single step method of RNA isolation by acid guanidinium thiocyanate-phenyl-chloroform extraction." in Anal Biochem 1987; 162:159-69) and mRNA isolated by the method of Aviv and Leder (see Aviv H and Leder P. "Purification of biologically active globin MRNA by chromatography on oligothymidylic acid-cellulose." in PNAS 1972;62:1408-12). For Northern analysis of PBEF gene expression in fetal membranes obtained before and after the onset of labor at preterm (25-35 weeks gestation) and term (39-41 weeks gestation), numerous tissue samples (24) were collected and divided into four groups for analysis:

preterm labor (n=5), preterm Cesarean section without labor (n=6) performed due to intrauterine growth restriction, pre-eclampsia or abdominal trauma, term labor (n=6), and elective term Cesarean section without labor (n=7).

For the Northern analysis of IL-6 and IL-8 gene expression after rhPBEF treatment, fetal membranes from elective term Cesarean sections before labor (37-40 weeks gestation, n=6) were collected and cut into 3×3 cm explants. None of the preterm or term patients or tissues had any clinical or histological signs of chorioamnionitis. The placentas and membranes were examined by a pathologist for histological evidence of infection using the criteria of Naeye (see Naeye R I. "Disorders of the placenta, fetus and neonate: diagnosis and clinical significance." St Louis: C U Mosby; 1992. p.258) and all tissues with any sign of infection were excluded from this study.

EXAMPLE 2

Immunolocalization

Tissue sections (7 μm) were cut and mounted on Vectabond-treated slides (Vector Laboratories, Burlingame, Calif.), deparaffinized and hydrated in deionized water. They were treated with 0.3% hydrogen peroxide in methanol for 30 min to block endogenous peroxidase activity and washed in PBS for 20 min. Sections were treated with normal goat serum (1.5%) for 20 min to block all non-specific binding sites and then incubated with the IgG fraction derived from a rabbit polyclonal antibody to human PBEF (see Samal et al., supra) at 5 μg/ml in 0.5% normal goat serum at room temperature for 30 min. The negative controls were adjacent sections processed with IgG fraction derived from normal rabbit serum at the same concentration as the primary antibody. The sections were rinsed three times in 0.015 M PBS, 6 min total, then incubated with a biotinylated secondary antibody for 30 min, rinsed three times in 0.015 M PBS, 6 min total and treated with the ABC reagent (Vector Laboratories) for 30 min and diaminobenzidine (0.5 mg/ml) at room temperature for 7 min. The sections were washed in distilled water, counterstained with hematoxylin, dehydrated and mounted in Pro-Texx (Baxter Scientific, Honolulu, Hi.), and viewed under bright field microscopy.

FIG. 1 demonstrates that the PBEF protein was immunolocalized in a consistent and uniform manner in the fetal membranes obtained in early pregnancy (87 days gestation; see FIG. 1A). Good staining was obtained in the amniotic epithelium and mesenchymal cells of the amniotic connective tissue in each tissue studied. A consecutive section was used as a control with IgG derived from non-immune rabbit serum at the same concentration (see FIG. 1B). The fetal membranes from patients delivered preterm, after labor, showed positive staining for PBEF (which was also uniform over each section), with no evidence of chorioamnionitis. The staining was primarily in the amniotic epithelium, with good staining also in the cells of the chorionic cytotrophoblast and the parietal decidua. The decidual cells are not easily seen in this section, but also stained quite well (see FIG. 1C). Normal fetal membranes from a term spontaneous labor and delivery shows good staining in the amniotic epithelial cells, which appeared to be perinuclear in many cells. The mesenchymal cells embedded in the connective tissue of the amnion and chorion were quite prominently stained in this section. There was also uniform staining of the cytoplasm of the cells of the chorionic cytotrophoblast and the decidua; the latter is not seen in this section (see FIG. 1D).

EXAMPLE 3

Northern Analysis

Total RNA was extracted (see Chomzynski and Sacchi, supra) and MRNA prepared as previously described (see Aviv and Leder, supra). Samples of MRNA (10-20 μg) were electrophoresed, and the RNA transferred to a nylon membrane (Magna Graph, MSI, Westborough, Mass.) as previously described (see Ognjanovic et al., supra). The cDNA probes were labeled using the Random Primed DNA labeling kit and following the manufacturer's instructions (Invitrogen, Carlsbad, Calif.). The filters were hybridized at 68° C. for 1 h using Express Hyb solution (Clontech, Palo Alto, Calif., USA). A final wash stringency of 0.1×SSC, 0.1% SDS was performed at 50° C. Filters were deprobed in 0.5% SDS for 10 min at 100° C. and re-hybridized sequentially with cDNA probes to PBEF, IL-6 and IL-8 and finally with a human glyceraldehyde-3 phosphate dehydrogenase (G3PDH) cDNA probe (Clontech), as an internal standard. The Northern blot was quantitated with a Phospholmager (Amersham Pharmacia Biotech, Piscataway, N.Y.), using the G3PDH value for each sample to standardize sample loading. Results were expressed as a ratio to G3PDH. Statistical analysis was performed using the Tukey-Kramer multiple comparison test.

The cDNA probes for PBEF (600 bp) and for IL-6 (639 bp) were both prepared as previously described (see Nemeth I, supra; and Millar K, Boesche M H, Yamamoto S Y, Killeen J DeBuque L, and Chen R et al. "A relaxin-mediated pathway to the preterm premature rupture of the fetal membranes, independent of infection." in Am J Obstet Gynecol 1998;179: 126-34). The IL-8 cDNA probe was a generous gift from Dr. Kouji Matsushima, Cancer Center, Kanazawa, Japan.

EXAMPLE 4

Recombinant Human PBEF Protein Production rhPBEF was produced in a bacterial system using pTrcHis2 vector (Invitrogen, Carlsbad, Calif.). PBEF was amplified by polymerase chain reaction (PCR) from a library prepared from fresh human amnion, chorion and decidua with 5' and 3' primers:

```
CAACAAGAATTCATGAATCCTCGCGCAGAAG,        (SEQ ID NO:1)
and

CTTAAGCGCCGGCGATGATGTGCTGCTTCCAGTTC,    (SEQ ID NO:2)
``` respectively. The PCR product was subcloned in the pTrcHis2 vector and positive colonies were identified by colony lift. One clone was sent for sequencing at the University of Hawaii Biotechnology Facility and the rhPBEF sequence was confirmed. The production of the rhPBEF protein was carried out following the Invitrogen pcDNA 3.1/V5-His TOPO TA Cloning Kit protocol. Briefly, a single colony was used to inoculate Luria-Bertani (LB) media and the culture was incubated until the optical density at $OD_{600}$ reached 0.6, when rhPBEF production was induced with 50 mM isopropyl β-D-thiogalactopyranoside (IPTG). It was stopped after 8h, the cells were then collected by centrifugation and lysed by freeze-thawing (alternating methanol-dry-ice and 37° C. waterbath). The lysates were spun, filtered through 0.8 μm syringe filters and stored at −20° C. The rhPBEF protein was purified using ProBond resin from Xpress System Protein Purification (Invitrogen) according to the manufacturer's manual. Briefly, the resin was equilibrated with native binding buffer (20 mM phosphate buffer, 500 mM NaCl, pH 7.8) and the lysates loaded. The washes were carried out in native wash buffer (20 mM phosphate buffer, 500 mM NaCl, pH 6.0) and rhPBEF was eluted with 350 mM imidazole. All eluates were collected, imidazole was replaced with 50 mM sodium phosphate buffer pH 7.2 and concentrated using Centricon Plus-20 filtration units (Millipore Corporation, Bedford, Mass.). The concentration of rhPBEF was determined using the BioRad Protein Assay (BioRad Laboratories, Hercules, Calif.). An aliquot (50 μg) was kindly sequenced by Dr E. Petricoin, FDA/NIH Washington DC, and six separate peptides confirmed its identity. In addition, an aliquot was assayed for lipopolysaccharide content by Biowhittaker Inc. (Walkersville, Md.). This showed a concentration of 0.03 EU/ng, well below the acceptable limit of 10 EU/ng.

EXAMPLE 5

Amnion-Like Epithelial (WISH) Cell Culture and Treatment

The amnion-like epithelial (WISH) cells were obtained from American Type Culture Collection (ATCC# CCL-25) (ATCC, Manassas, Va.). WISH cells were cultured in Dulbecco's Modified Eagle Medium:Ham F-12 (DMEM:F12) (1:1) supplemented with 10% fetal bovine serum (FBS) (Life Technologies, Grand Island, N.Y.), penicillin (50 U/ml)-streptomycin (50 μg/ml) and incubated at 37° C. in 5% $CO_2$/95% air. After reaching confluency, the cells were trypsinized and plated into 6-well culture dishes at a density of $1 \times 10^5$ cells in 4 ml media. After 48 h or when the cells reached 80% confluency, the growth medium was replaced with minimal media (0.5% FBS and 0.2% lactalbumin in DMEM:F12) and incubated for 12 h. Treatment of the cells began with addition of rhPBEF prepared in minimal media. The concentration of rhPBEF was determined using the BioRad protein assay and 1, 10 and 100 ng/ml was added to the cells for 4 and 24 h. Treatment was carried out in triplicate and each experiment was performed at least three times on different occasions. Controls received minimal media containing 0.5% bovine serum albumin (15 μl) in phosphate buffer saline (PBS). After treatment of the cells, the media was collected and stored frozen at −20° C. and the cells lysed in 1 ml Trizol reagent (Life Technologies, Grand Island, N.Y.). Total RNA was isolated from the lysates following the manufacturer's protocol.

EXAMPLE 6

Northern Analysis of PBEF in the Fetal Membranes, Decidua and Placenta

Figure 2:
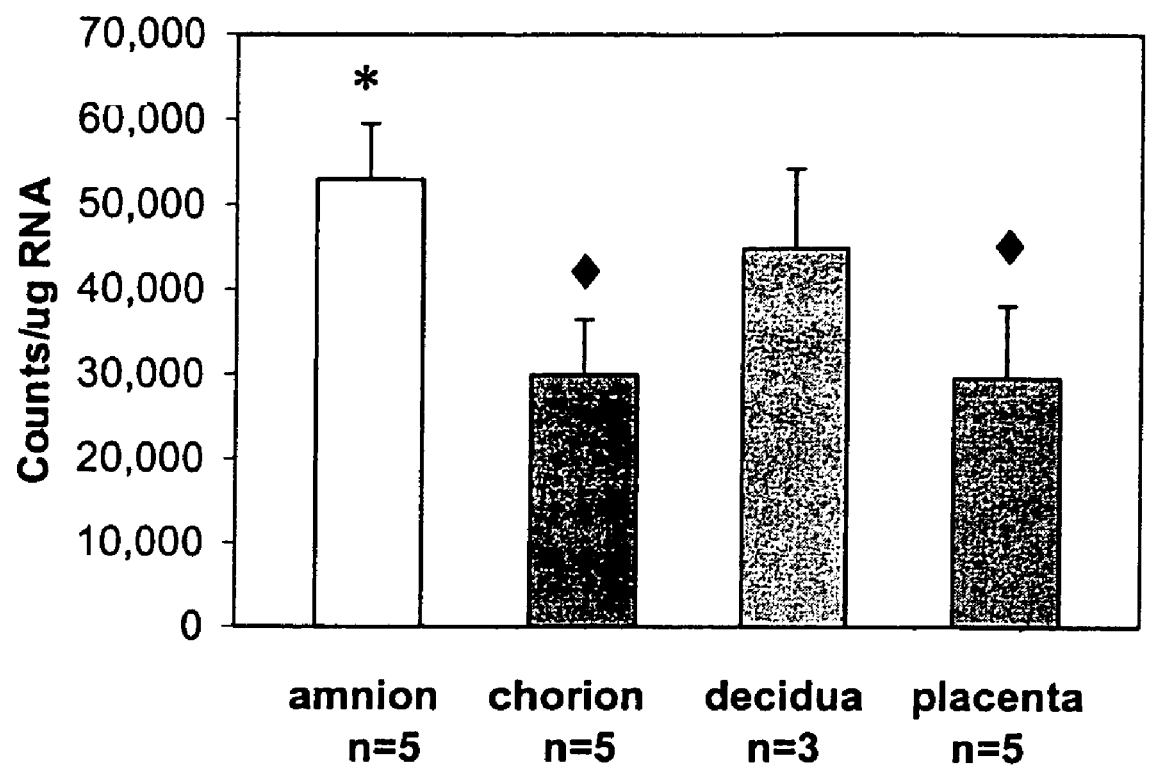
FIG. 2 presents quantitative Northern analysis of PBEF gene expression in the fetal membranes and placenta, expressed as counts/µg. *There was significantly more ($p<0.01$) PBEF expressed in the amnion compared to the chorion or placenta.

A Northern blot with separated amnion, chorion, decidua and placental trophoblast obtained at term prior to labor and delivery shows that all three PBEF transcripts of 2.0, 2.4 and 4.0 kb, when quantitated separately, were expressed in each of the different tissues in similar proportions. All transcripts were therefore included in the quantitation. Some of the samples showed stronger hybridization of all transcripts than did others, in spite of equal loading of the RNA. The quantitation of this blot is shown in FIG. 2, expressed as counts/μg RNA, due to lack of a suitable housekeeping gene, which can be used with both membranes and placenta. There was significantly more ($p<0.01$) PBEF expressed in the amnion than in either the chorion or the placenta.

EXAMPLE 7

Figure 3A:
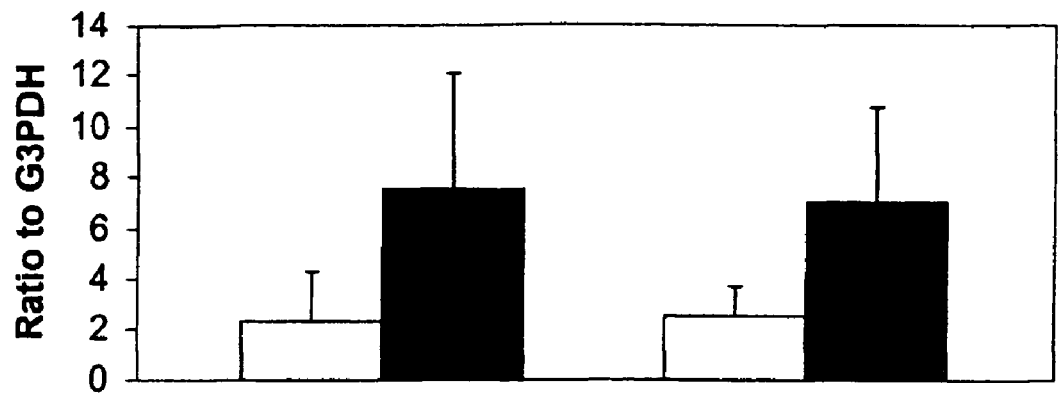
FIG. 3A illustrates that PBEF expression was upregulated by labor, but this did not reach significance at either gestational age.
Figure 3B:
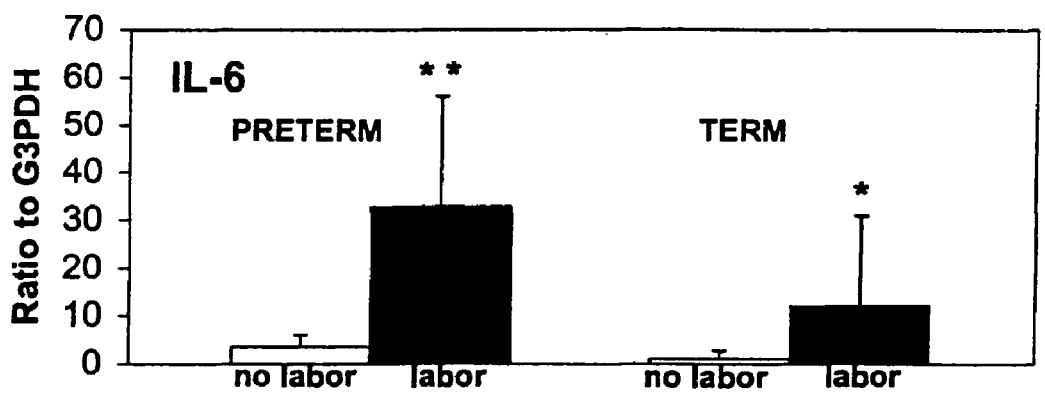
FIG. 3B illustrates that IL-6 expression after labor and delivery was significantly upregulated both at preterm and term compared to the non-labored tissues of matched gestational age * ($p<0.01$ in each case). IL-6 expression at preterm labor was ** significantly higher than that at term labor ($p<0.05$). The correlation between PBEF and IL-6 expression ($r=0.64$) was significant ($p<0.1$), and that between PBEF and IL-8 expression ($r=0.86$) was also extremely significant ($p<0.0001$).
Figure 3C:
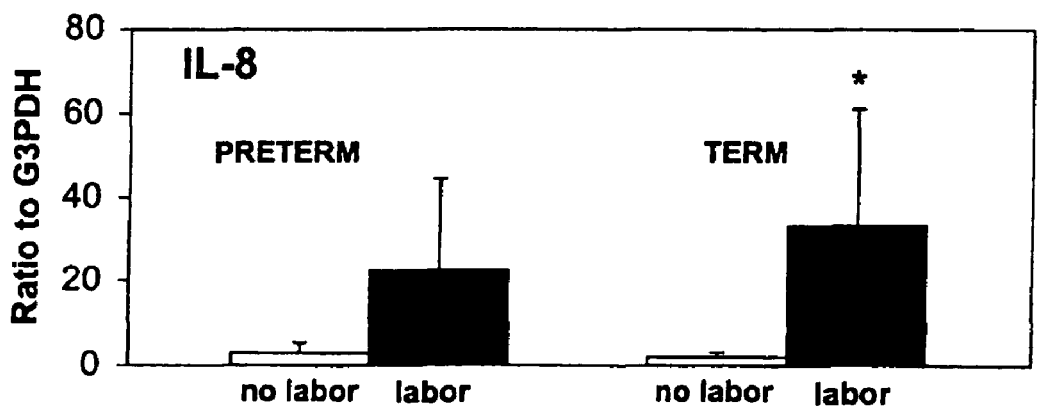
FIG. 3C illustrates that IL-8 expression was increased after labor both at preterm and term, where the latter reached statistical significance * ($p<0.05$) when compared to the non-labored tissues of matched gestational age.

Northern Analysis of PBEF, IL-6 and IL-8 Before and After the Onset of Labor at Preterm and Term In the absence of labor, PBEF was constitutively expressed at similar levels in both preterm and term fetal membranes. The process of labor caused upregulation of PBEF expression to the same extent both at preterm and term when compared to the respective non-labored group, but this upregulation was not significant due to the large patient-to-patient variability in the non-labored group. The basal levels of IL-6 and IL-8 expression, in the absence of labor (and regardless of gestational age) were lower than those of PBEF, and labor acted as a stronger inducer of their expression (see FIGS. 3A-3C). This resulted in a significant increase of IL-6 expression after labor and delivery both at preterm and term compared to the non-labored tissues of matched gestational age ($p<0.01$ in each case). IL-6 expression increased significantly more with preterm than with term labor ($p<0.05$). IL-8 expression was significantly increased only after term labor ($p<0.05$) compared to non-labored term tissues. Comparison of IL-8 expression in preterm tissues with and without labor showed an increase, which did not reach significance. In spite of the greater patient variability of PBEF expression, there was a good correlation between PBEF and IL-8 ($r=0.87$).

EXAMPLE 8

The Effects of PBEF on the Expression of IL-6 and IL-8 in WISH Cells and Fetal Membrane Explants Fetal Membrane Explant Treatment. Each fetal membrane was cut into several 3×3 cm explants. One explant was used to check for infection and another was treated with 100 ng/ml rhPBEF in minimal media for 4 h, an adjacent explant was used as a control and incubated in minimal media only. Total RNA was isolated using the RNeasy Maxi kit (Qiagen Inc., Valencia, Calif.) according to the manufacturer's protocol and used for Northern analysis.

Figure 4A:
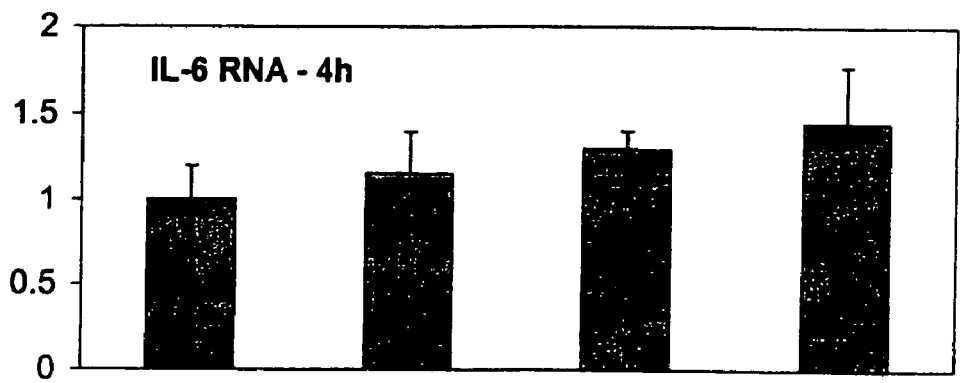
FIG. 4A illustrates the dose-dependent increase in IL-6 gene expression after treatment with rhPBEF at 1, 10 and 100 ng/ml for 4h. *Significantly ($p<0.05$) increased expression compared to the control.
Figure 4B:
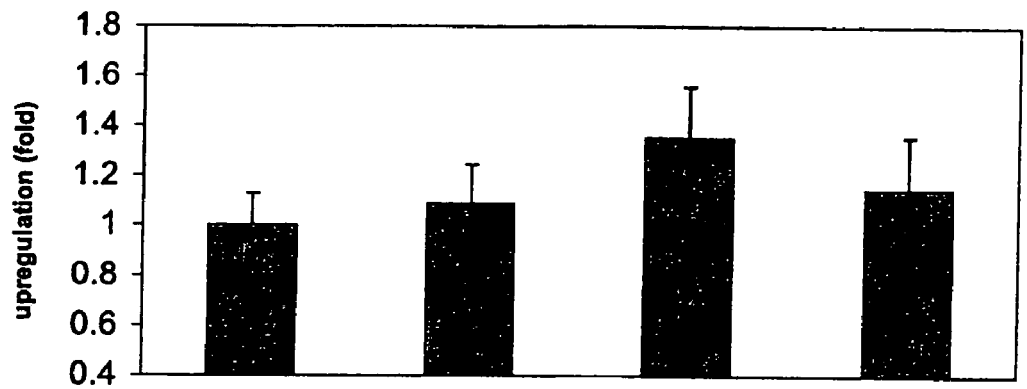
FIG. 4B illustrates the dose-dependent effect of rhPBEF on IL-8 gene expression: 10 ng/ml rhPBEF caused a significant ($p<0.01$) increase in IL-8 gene expression after 4h.
Figure 4C:
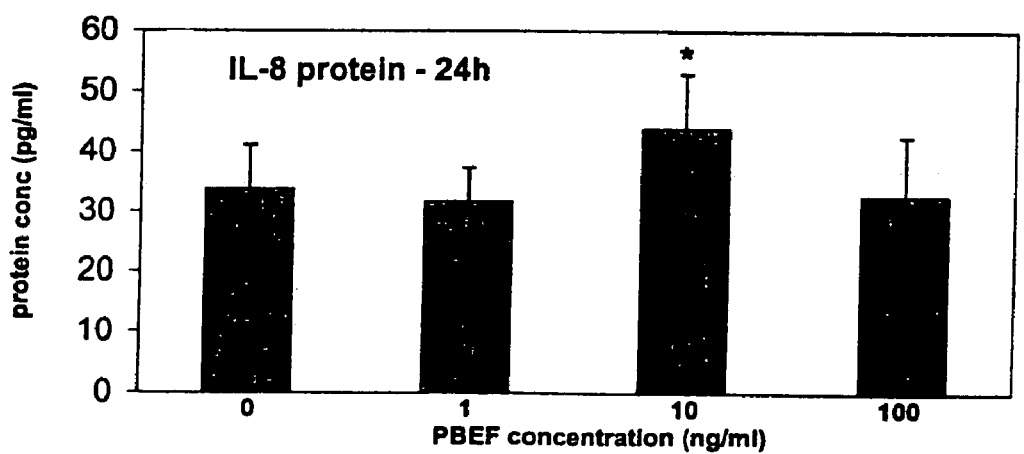
FIG. 4C illustrates the effect of rhPBEF on IL-8 protein expression in the media after 24 h of treatment measured by ELISA: 10 ng/ml rhPBEF caused a significant ($p<0.01$) increase, compared to the control.
Figure 5:
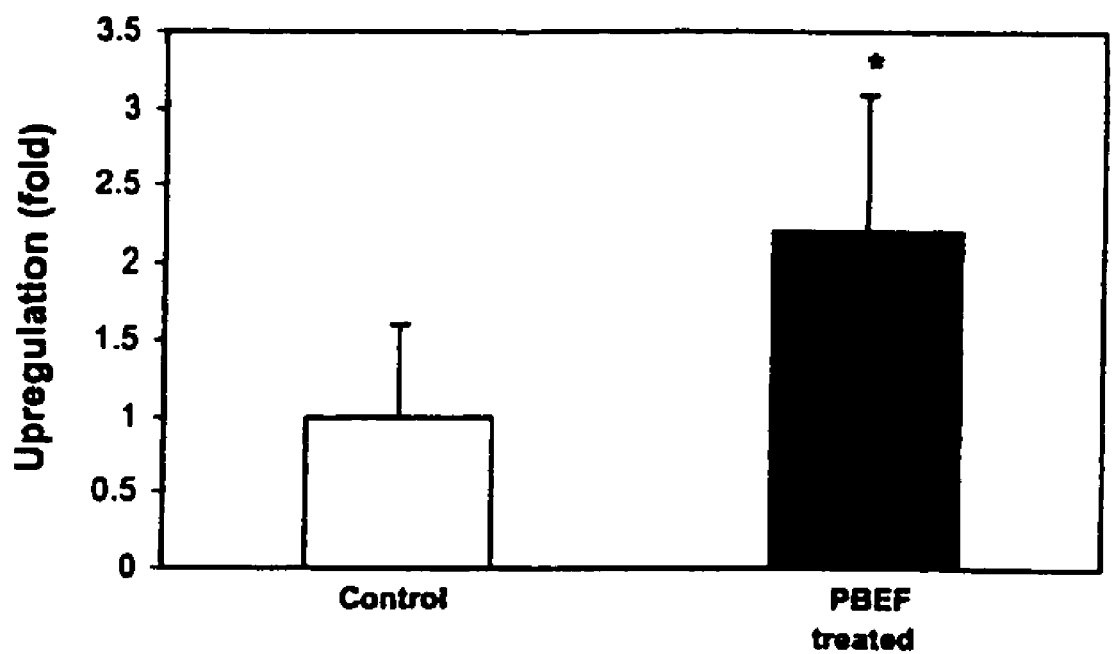
FIG. 5 demonstrates the effect of rhPBEF treatment on the expression of IL-8 in fetal membrane explants. RhPBEF (100 ng/ml) caused *significant ($p<0.05$) increase in IL-8 gene expression after 4 h of treatment, compared to the control.

In addition to fetal membrane explants, the amniotic epithelial cell line, WISH cells, were also used to study the effects of PBEF on the expression of IL-6 and IL-8. The expression of the IL-6 and IL-8 genes were quantitated by Northern blotting using total RNA isolated from the cells and calculated as the degree of upregulation (fold) compared to the respective control at each time (see FIGS. 4A-4C). The treatment of WISH cells with rhPBEF caused a dose-dependent increase (15, 29 and 44%, respectively) in IL-6 gene expression after 4 h with both 10 and 100 ng/ml which were both significant (p<0.05) (FIG. 4A). The treatment with 10 ng/ml rhPBEF caused a 35% increase in IL-8 gene expression after 4 h of treatment, which was significant (p<0.01), this effect was absent with 100 ng/ml (FIG. 4B). The IL-8 protein levels in the media showed a basal expression level of 34 pg/ml which remained the same at 4h and 24h (data not shown). The 10 ng/ml dose of rhPBEF caused a small (15%) increase in secreted IL-8 after 4 h (p<0.05) (not shown) and a greater increase (30%) after 24 h treatment (p<0.01) which reached significance (FIG. 4C). Thus, the same dose of rhPBEF (10 ng/ml) increased expression of both the IL-8 gene and protein. Fetal membrane explants were also treated with rhPBEF, since WISH cells are an amnion-derived cell line. Explants were treated with the highest dose (100 ng/ml) of rhPBEF because it was anticipated that more would be required with tissue to show an effect. The expression of the IL-6 and IL-8 genes were quantitated by Northern analysis and the results for the latter are shown in FIG. 5. rhPBEF treatment caused a 40% upregulation of IL-6 and 120% upregulation of IL-8 gene expression when compared to the control (p<0.0I and p<0.05, respectively). The statistical analysis was performed using the Wilcoxon matched pairs test.

Figure 6:
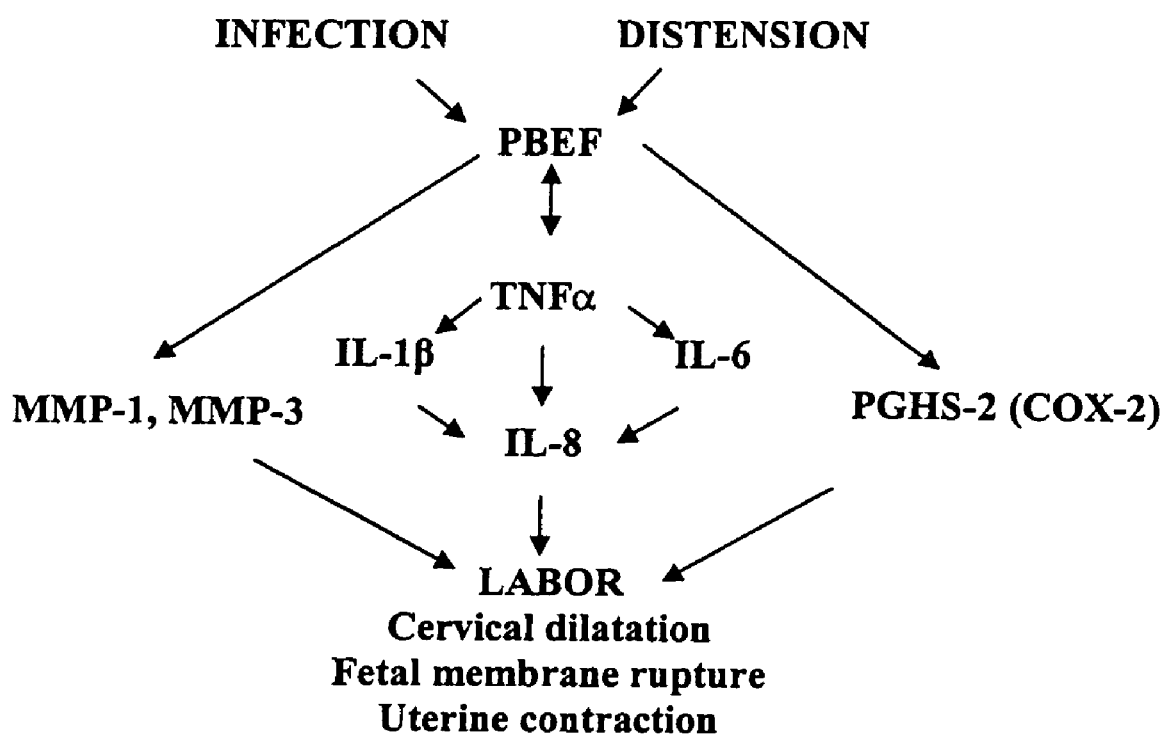
FIG. 6 presents a diagrammatic summary of the possible relationships between PBEF, TNF-α, IL-1β, IL-6 and IL-8, and their controls by mechanical distension and by infection leading to labor.

FIG. 6 is a diagrammatic summary of how distension and infection causing PBEF to be upregulated is currently believed to influence the key molecules involved in human birth.

EXAMPLE 9

Enzyme-Linked Immunosorbent Assay

The IL-8 enzyme-linked immunosorbent assay (ELISA) kit was purchased from R&D Systems (Minneapolis, Minn.) and used to determine the IL-8 protein concentration in the culture supernatants following the manufacturer's protocol. The sensitivity of the assay was 15 pg/ml. The basal levels of IL-6 protein in conditioned media of WISH cells were reported to be at the limit of sensitivity of ELISA (see Keelan et al., supra) and could not be considered reliable, therefore the levels of IL-6 protein were not measured.

EXAMPLE 10

The Effects of PBEF on the Expression of Key Mediators of Labor in Fetal Membrane Explants by Gene Chip Analysis Fetal Membrane Explant Treatment. Fetal membranes from three patients were cut into several 3×3 cm explants. One explant was used to check for infection. Another explant was treated with 100 ng/ml rhPBEF in minimal media for 4 hours, an adjacent explant was used as a control and was incubated in minimal media only for the same period. At the end of this time, total RNA was extracted using the RNeasy Maxi kit (Qiagen Inc., Valencia, Calif.). These RNAs were run in pairs (explants treated and controls from each of the patients), were reverse-transcribed and the resulting cDNAs/cRNAs labeled with tracking fluorescent dyes and hybridized to DNA microchips (Affymetrix Inc.) containing 22,000 gene transcripts. The binding of the fluorescent fragments was proportional to the abundance of the gene in the original samples. Therefore changes in gene expression result in signal differences. Computer analysis of the signals and application of a number of these computer algorithms have allowed the identification of seven genes, which consistently increased in all patients after the in vitro PBEF treatment. The Affymetrix system has numerous controls built into the methodology in order to minimize false positive results. Thus, the genes identified as significantly upregulated were: TNF-$\alpha$, IL-1$\beta$, IL-6, MIP-1$\alpha$, MIP-1$\beta$, GRO-$\gamma$ and COX-2.

Confirmation of these gene studies was undertaken in a second set of tissue explants obtained from different patients, as well as in those used in the primary Affymetrix study. In order to confirm these results, the secreted proteins into the media have been assayed by specific ELISAs, if these were commercially available, or by real-time RT-PCR for the genes if ELISA was not appropriate or available. All have been shown to be significantly upregulated, thus confirming the Affymetrix gene chip study.

The results of this example show that PBEF is the most upstream player capable of stimulating the key proteins known to be in the cascade of events leading to labor in women.

EXAMPLE 11

PBEF Assays

PBEF levels can be measured in biological samples in a variety of ways. For example, an ELISA can be carried out using antibodies raised against recombinant human PBEF or against synthetic peptides derived from PBEF and raised in sheep, against recombinant human PBEF or synthetic peptides based on PBEF and raised in rabbits, against recombinant human PBEF or against synthetic peptides based on PBEF and raised in chickens, and the like.

In one aspect, the ELISA can be carried out in a competitive format by coating ELISA plates with anti-PBEF antibodies, blocking the non-specific sites with blocking buffer and incubating them with different amounts of biotinylated recombinant human PBEF protein (biotin-rhPBEF) to provide the standard curve. Experimental samples or unknowns are then diluted sequentially and added to the known amount of biotin-rhPBEF. The standards and unknowns are then incubated with streptavidin-conjugated horseradish peroxidase (HRPO) and the amount of biotin-rhPBEF detected by color development with a color forming compound such as 2,2-azino-bis(3-ethylbenzthiazoline-6 sulfonic acid). Displacement of the biotin-rhPBEF by the PBEF protein is measured by the amount of color developed—the color is directly related to the amount of PBEF present in the sample. The amount of PBEF in the unknown samples can then be quantitated against the standard curve.

If desired, the sensitivity of the above-described assay can be enhanced by such techniques as signal amplification, use of alkaline phosphatase (in place of HRPO), along with a fluorescent substrate such as 4-methylumbelliferyl phosphate, and the like.

EXAMPLE 12

Determination of Transcription Factors Involved in the Inflammatory and Stretch Induced Stimulation of PBEF Pre-B-cell colony enhancing factor (PBEF) is a highly conserved 52 kDa pro-inflammatory cytokine with poorly understood biological activities. However, it has been shown to be up-regulated after labor at preterm and term, in the absence of infection and by distension of the fetal membranes (Nemeth et al., Amer J Obstet Gynecol 2000: 182: 50-59). Inflammatory mediators also increase PBEF gene expression (Ognjanovic et al., J Mol Endocrinol 2001: 26: 107-117). Gene promoter analysis of PBEF identified several putative regulatory elements, suggesting that it may be chemically and mechanically responsive to several inducers of transcription.

PBEF expression. It has further been established that PBEF causes NF-κB to be upregulated—which causes a feed-forward loop, that spirals once started, and therefore represents one mechanism of starting labor.

While the invention has been described in detail with reference to certain preferred embodiments thereof, it will be understood that modifications and variations are within the spirit and scope of that which is described and claimed.

```
                              SEQUENCE LISTING

<160> NUMBER OF SEQ ID NOS: 2

<210> SEQ ID NO 1
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
caacaagaat tcatgaatcc tcgcgcagaa g                                    31

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cttaagcgcc ggcgatgatg tgctgcttcc agttc                                35
```

Thus, the human amniotic epithelial-like cell line (WISH) was stimultated by addition of IL-1β (1 ng/ml) or by stretching (20%). In order to show any inhibitory effects on the expression of PBEF, a panel of inhibitors (SN50, Curcumin and PDTC) were added over a range of dilutions to both systems. Gene expression was quantitated by real-time PCR and normalized to 18 s.

Peak translocation of NF-κB from the cytoplasm to the nucleus occurred one hour after addition of IL-1β and was clearly seen by immunolabeling with an antibody (anti-p65) to one of the subunits of NF-κB. Increased PBEF gene expression also resulted from IL-1β stimulation. When the specific inhibitor of NF-κB (SN50 60 μM) was added together with IL-1β, the increase in PBEF expression was completely abolished. Antioxidant inhibitors (Curcumin and PDTC), with no specific transcriptional target, also prevented the up-regulation of PBEF to varying degrees. These data suggest that several transcription factors have regulatory roles in the response of PBEF to an inflammatory stimulus.

The results presented herein demonstrate that NF-κB is involved as a transcription factor in the cascade of cell signaling events that leads to PBEF expression during an inflammatory response and is also likely to be involved in its response to stretching. The demonstration of the role of NF-κB in both stimuli leading to transcription of PBEF suggest that both inflammation and stretching induce PBEF expression by similar pathways.

Since an inflammatory response in these tissues is associated with labor in women, and labor, distension and infection all cause an increase in the transcription factor NF-κB in the amnion and myometrium, it has, therefore, been demonstrated that NF-κB is involved in the events which lead to That which is claimed is:

1. A method for determining whether a subject has commenced labor, said method comprising assaying for the level of pre-B cell colony-enhancing factor (PBEF) in one or more of the serum, cervical fluid, vaginal fluid and amniotic fluid of said subject, and identifying a subject whose level of PBEF is elevated above baseline as having commenced labor.

2. The method of claim 1 wherein said subject is suspected of having commenced preterm labor.

3. The method of claim 1 wherein the level of PBEF is assayed by immunoassay.

4. The method of claim 1 wherein the level of PBEF is assayed by lysate array.

5. The method of claim 1 wherein the level of PBEF is assayed by chromatographic analysis.

6. The method of claim 1 wherein the level of PBEF is assayed by mass spectrometric analysis.

7. The method of claim 1 wherein said method comprises assaying for the level of PBEF in the serum of said subject.

8. The method of claim 1 wherein said method comprises assaying for the level of PBFF in the cervical fluid of said subject.

9. The method of claim 1 wherein said method comprises assaying for the level of PBEF in the vaginal fluid of said subject.

10. The method of claim 1 wherein said method comprises assaying for the level of PBEF in the amniotic fluid of said subject.

* * * * *

UNITED STATES PATENT AND TRADEMARK OFFICE
CERTIFICATE OF CORRECTION

| | | |
|---|---|---|
| PATENT NO. | : 7,524,636 B2 | Page 1 of 1 |
| APPLICATION NO. | : 11/112659 | |
| DATED | : April 28, 2009 | |
| INVENTOR(S) | : Gillian D. Bryant-Greenwood et al. | |

It is certified that error appears in the above-identified patent and that said Letters Patent is hereby corrected as shown below:

On Column 1, line 2, please insert the following heading and paragraph:

--ACKNOWLEDGEMENT

This invention was made with government support under Grant No. 5R01 HD024314, awarded by the National Institute of Health; under Grant No. 5P20RR011091, awarded by the National Institute of Health; and under Grant No. IP20RR016467, awarded by the National Institute of Health. The government has certain rights in the invention.--

Signed and Sealed this

Fourteenth Day of July, 2009

JOHN DOLL
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 7,524,636 B2 | Page 1 of 1 |
| APPLICATION NO. | : 11/112659 | |
| DATED | : April 28, 2009 | |
| INVENTOR(S) | : Bryant-Greenwood et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 535 days.

Signed and Sealed this
Nineteenth Day of April, 2011

David J. Kappos
*Director of the United States Patent and Trademark Office*